United States Patent
Bohlmann et al.

[11] Patent Number: 5,502,046
[45] Date of Patent: Mar. 26, 1996

[54] 11β-SUBSTITUTED 14,17-ETHANOESTRATRIENES, PROCESS FOR THEIR PRODUCTION AND THEIR USE AS PHARMACEUTICAL AGENTS

[75] Inventors: Rolf Bohlmann; Hermann Kunzer; Hans-Peter Muhn-Seipoldy; Yukishige Nishino; Martin Schneider, all of Berlin, Germany

[73] Assignee: Schering Aktiengesellschaft, Berlin, Germany

[21] Appl. No.: 211,173

[22] PCT Filed: Sep. 24, 1992

[86] PCT No.: PCT/EP92/02210

§ 371 Date: Jun. 24, 1994

§ 102(e) Date: Jun. 24, 1994

[87] PCT Pub. No.: WO93/06124

PCT Pub. Date: Apr. 1, 1993

[30] Foreign Application Priority Data

Sep. 24, 1991 [DE] Germany .................. 41 32 182.0

[51] Int. Cl.⁶ .................. A61K 31/565; C07J 1/00
[52] U.S. Cl. .................. 514/182; 552/626
[58] Field of Search .................. 552/626; 514/182

[56] References Cited

U.S. PATENT DOCUMENTS 4,272,530 6/1981 Teutsch et al. .................. 552/626
4,547,493 10/1985 Teutsch et al. .................. 552/626
4,943,566 7/1990 Nedelec et al. .................. 552/626
5,134,136 7/1992 Kirsch et al. .
5,145,847 9/1992 Bohlmann et al. .

FOREIGN PATENT DOCUMENTS 0372665 6/1990 European Pat. Off. .
0410554 1/1991 European Pat. Off. .
0430386 6/1991 European Pat. Off. .

*Primary Examiner*—Kimberly J. Kestler
*Attorney, Agent, or Firm*—Millen, White, Zelano, & Branigan

[57] ABSTRACT

The invention relates to 11 β-substituted 14,17-ethanoestratrienes of the general formula 1

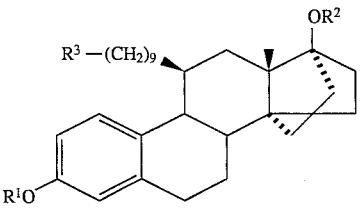

where $R^1$, $R^2$ and $R^3$ are defined in the specification. The compound have antiestrogenic activity and are, therefore, useful for the treatment of estrogen dependent disorders.

17 Claims, No Drawings

11β-SUBSTITUTED 14,17-ETHANOESTRATRIENES, PROCESS FOR THEIR PRODUCTION AND THEIR USE AS PHARMACEUTICAL AGENTS

This application is a 371 of PCT/EP92/02210 filed Sep. 24, 1992, now abandoned.

This invention relates to 11β-substituted 14,17-ethanoestratrienes of general formula I

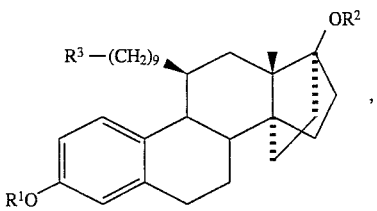

in which $R^1$ stands for a hydrogen atom, a $C_1$–$C_{12}$ alkanoyl, a benzoyl, a straight-chain or branched-chain $C_1$–$C_{12}$ alkyl, a $C_3$–$C_7$cycloalkyl or a $C_4$–$C_8$ alkylcycloalkyl group, $R^2$ stands for a hydrogen atom or a $C_1$–$C_{12}$ alkanoyl group and $R^3$ stands for a grouping

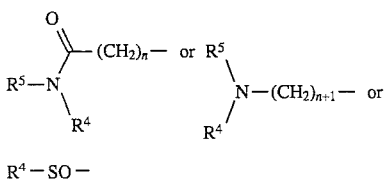

in which n is 0, 1 or 2, and $R^4$ and $R^5$ independently of one another, mean a hydrogen atom or a straight-chain or branched $C_1$–$C_8$ alkyl group, which can also be present partially fluorinated, a process for their production, pharmaceutical preparations containing these compounds, as well as their use for the production of pharmaceutical agents.

If $R^1$ and/or $R^2$ stand for an alkanoyl group, first of all an acetyl or propionyl group is considered; for $R^1$ in the meaning of an alkyl group, above all the methyl or ethyl groups are suitable As cycloalkyl group for substituent $R^1$ for example, the cyclopropyl, cyclopentyl and cyclohexyl group and as alkylcycloalkyl group, the methylcyclopropyl and methylcyclopentyl group are to be mentioned.

As partially fluorinated alkyl groups $R^4$ and $R^5$, first of all radicals 2,2,3,3,4,4,4-heptafluorobutyl and 4,4,5,5,5-pentafluoropentyl are suitable.

Within the meaning of the invention, especially preferred compounds are:

11-(14,17-Ethano-3,17-dihydroxyestra-1,3,5(10)-trien-11βyl)-undecanoic acid-(N-methyl-N-isopropyl)-amide, 11-(14,17-ethano-3,17-dihydroxyestra-1,3,5(10)-trien-11β yl)-undecanoic acid-(N-methyl-N-2,2,3,3,4,4,4-heptafluorobutyl)amide, 14,17-ethano-11β-(11-N-methyl-N-isopropylaminoundecyl)-estra 1,3,5(10)-triene-3,17-diol, 9-(14,17-ethano-3,17-dihydroxyestra-1,3,5(10)-trien-11β-yl)-nonyl-4,4,5,5,5-pentafluoropentyl-sulfoxide, 10-(14,17-ethano-3,17-dihydroxyestra-1,3,5(10)-trien-11β-yl)-decanoic acid-(N-methyl-N-isopropyl)-amide, 12-(14,17-ethano-3,17-dihydroxyestra-1,3,5(10)-trien-11β yl)-dodecanoic acid-(N-methyl-N-isopropyl)-amide, 11-(3-benzoyloxy-14,17-ethano-17-hydroxyestra-1,3,5(10)-trien-11β-yl)-undecanoic acid-(N-methyl-N-isopropyl)-amide, 11-(14,17-ethano-17-hydroxy-3-methoxyestra-1,3,5(10)-trien-11β-yl)-undecanoic acid-(N-methyl-N-isopropyl)-amide.

Steroidal antiestrogens, which are essentially free of an estrogenic residual effect (pure antiestrogens), follow from EP-A 0 138 504 and EP 0 384 842. From the plurality of substances described in EP-A 0 138 504, especially the 11-(3,17β-dihydroxy-1,3,5(10)-estratrien-7α-yl)-undecanoic acid-(N-butyl-N-methyl)amide is to be emphasized.

An increase of the estrogenic effectiveness relative to estradiol in peroral administration by introducing a 14,17-ethano bridging-over was observed in the 14,17-ethanoestratrienes described in international patent application WO 88/01 275, which carry two hydrogen atoms each as substituents on the C-7 and C-11 atom.

It has now been found that the compounds of general formula I according to the invention exhibit an especially high affinity to the estrogen receptor and, in the case of peroral administration, they are pure antiestrogens with very strong antiestrogenic effect.

The compounds according to the invention thus are suitable for treatment of estrogen-dependent diseases, for example, anovulatory infertility, prostatic hyperplasia, breast cancer, endometrial cancer and melanoma.

The daily dose for treating said diseases is typically 0.1 to 25 mg/kg; in humans, this corresponds to a daily dose of 5 to 1250 mg. According to the invention, a dosage unit contains 5 to 500 mg of one or more compounds of general formula I.

The compounds according to the invention are suitable for the production of pharmaceutical compositions and preparations. The pharmaceutical compositions or pharmaceutical agents contain as active ingredient one or more of the compounds according to the invention, optionally in a mixture with other pharmacologically or pharmaceutically effective substances. The production of the pharmaceutical agents takes place in a known way, and the known and usual pharmaceutical adjuvants as well as other usual vehicles and diluents can be used.

As such vehicles and adjuvants, for example, those are suitable that are recommended or indicated in the following bibliographic references as adjuvants for pharmacy, cosmetics and related fields: Ullmans Encyklopädie der technischen Chemie [Ullmans Encyclopedia of Technological Chemistry], Volume 4 (1953), pages 1 to 39; Journal of Pharmaceutical Sciences, Volume 52 (1963), pages 918 ff., H. v. Czetsch-Lindenwald, Hilfsstoffe für Pharmazie und angrenzende Gebiete [Adjuvants for Pharmacy and Related Fields]; Pharm. Ind., Number 2, 1961, page 72 ff.: Dr. H. P. Fiedler, Lexikon der Hilfsstoffe für Pharmazie, Kosmetik und angrenzende Gebiete [Encyclopedia of Adjuvants for Pharmacy, Cosmetics and Related Fields], Cantor KG. Aulendorf in Württemberg 1971.

The compounds can be administered orally or parenterally, for example, intraperitoneally, intramuscularly, subcutaneously or percutaneously. The compounds can also be implanted in the tissue. The amount of compound to be administered varies within a wide range and can cover every effective amount. As a function of the condition to be treated and the type of administration, the amount of administered compound can be 0.01–100 mg/kg of body weight, preferably 0.1–20 mg/kg of body weight per day.

For oral administration, capsules, pills, tablets, coated tablets, etc. are suitable. In addition to the active ingredient, the dosage units can contain a pharmaceutically compatible vehicle, such as, for example, starch, sugar, sorbitol, gelatin, lubricant, silicic acid, talcum, etc.

For parenteral administration, the active ingredients can be dissolved or suspended in a physiologically compatible diluent. As diluent, very often oils with or without adding a solubilizer, a surface-active agent, a suspending or emulsifying agent, are used. Examples for oils used are olive oil, peanut oil, cottonseed oil, soybean oil, castor oil and sesame oil.

The compounds can also be used in the form of a depot injection or an implant preparation, which can be formulated so that a delayed release of active ingredient is made possible.

As inert materials, implants can contain, for example, biodegradable polymers or synthetic silicones, such as, for example, silicone rubber. Furthermore, for percutaneous administration, the active ingredients can be incorporated, for example, in a plaster.

The compounds of general formula I are produced according to the invention, by a compound of general formula II

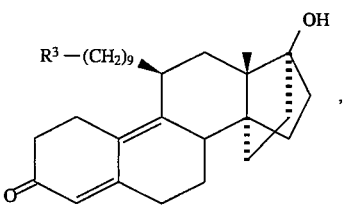 (II)

in which $R^3$ has the meanings indicated in formula I

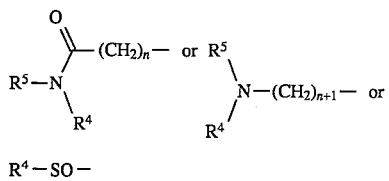

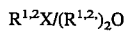

being aromatized with an acid halide/acid anhydride mixture $$R^{1,2}X/(R^{1,2'})_2O \qquad (III),$$

in which $R^{1,2}$ means a $C_1$–$C_{12}$ alkanoyl group and X means a chlorine or bromine atom, to the corresponding 1,3,5(10)-triene-3-hydroxy compound of general formula IV

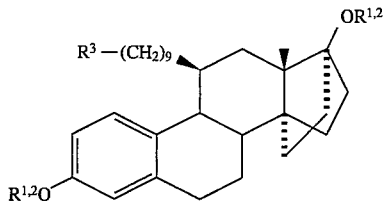 (IV)

and the latter then optionally being partially or completely saponified, optionally being partially esterified in 3-position or completely in 3- and 17-position with an acid halide or acid anhydride of general formula V

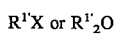 (V), in which $R^{1'}$ means a $C_1$–$C_{12}$ alkanoyl or benzoyl group and X means a chlorine or bromine atom, or being partially etherified in 3-position with an alkyl halide of general formula VI

 (VI), in which $R^{1''}$ means a straight-chain or branched-chain $C_1$–$C_{12}$ alkyl, a $C_3$–$C_7$ cycloalkyl or a $C_4$–$C_8$ alkylcycloalkyl group and Y means a chlorine, bromine or iodine atom, and optionally being esterified in 17-position with an acid halide or acid anhydride of general formula VII

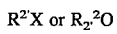 (VII), in which $R^{2'}$ means a $C_1$–$C_{12}$ alkanoyl group and X means a chlorine or bromine atom, and if $R^3$ stands for the carboxylic acid amide

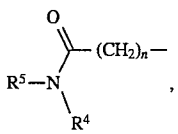

optionally its keto group being completely reduced.

The aromatization takes place with an acid halide/acid anhydride. The partial esterification or etherification of the 3-hydroxy group or the complete esterification of the 3- and 17hydroxy group takes place according to standard methods. The complete reduction of the keto group of the carboxylic acid amide can take place with lithium aluminum hydride or similar reducing agents according to also usual processes.

The following examples are used to explain the invention. Within the examples, the representation of the required compounds of general formula II as well as for the first time the representation of 4,4,5,5,5-pentafluoropentanol as well as its reaction to 4,4,5,5,5-pentafluoropentylmercaptan is also described. Further homologous fluoroalkanols for synthesis of further compounds according to the invention, in which $R^4$ represents a partially fluorinated alkyl group, can be obtained by analogous procedures.

3,3-(2,2-Dimethyltrimethylenedioxy)-5α, 10α-epoxy-14,17-ethano-estr-9(11)-en-17-ol (Scholz, S. et al., Liebigs Ann. Chem., (1989), p. 151 (13b)) is linked by the 9(11)-double bond under copper catalysis in 11-position with a Grignard reagent of formula

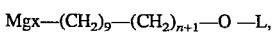

in which X is a chlorine, bromine or iodine atom, L is a hydroxy protecting group, such as, for example, the tert-butyldimenthylsily group and n is 0, 1 or 2 or MgX—$(CH_2)_9$—S—$R^4$, in which X has the above meaning and $R^4$ has the meaning indicated in formula I.

Then, the 4,9-dien-3-one structure is established by treating the Grignard addition product in moderately acid medium (for example, in a mixture of tetrahydrofuran and semi-concentrated acetic acid), and also optionally present terminal hydroxy protecting group L is cleaved. The ω-hydroxy group can then optionally be oxidized according to standard processes to the corresponding carboxylic acid (e.g., with Jones reagent). The ω-hydroxy group or carboxyl group is finally reacted with an amine H—$NR^4R^5$, in which $R^4$ and $R^5$ have the meaning indicated in formula I, to a compound of general formula II with a terminal amine or amide group in the 11β-alkyl substituent.

In the case of terminal function —S(O)—$R^4$, this sulfide must be oxidized to higher valency to corresponding sulfoxide —S—$R^4$, for example, with sodium periodate, to obtain a compound of the general formula.

EXAMPLE 1

11-(14,17-Ethano-3,17-dihydroxyestra-1,3,5 (10)-trien-11β-yl)-undecanoic acid-(N-methyl-N-isopropyl)-amide a) 11-Bromoundecyl-tert-butyldimethylsilyl ether 100 g of 11-bromoundecanol (Fluka) is dissolved in 240 ml of tetrahydrofuran and mixed at 25° C. with 58 g of imidazole as well as 74.3 g of tert-butyldimethylsilyl chloride in 80 ml of tetrahydrofuran and stirred for 2 hours at 25° C. For working up, 700 ml of diethyl ether is added, the precipitated hydrochloride is filtered off, evaporated to dryness in a vacuum and chromatographed on silica gel with hexane/toluene. 136.9 g of 11-bromoundecyl-tert-butyldimethylsilyl ether is obtained as oil.

b) 14,17-Ethano-11β-(11-hydroxyundecyl)-17-hydroxyestra-4,9-dien-3-one 7.2 g of magnesium chips is introduced in 70 ml of tetrahydrofuran and mixed with a solution of 108 g of 11-bromoundecyl-tertbutyldimethylsilyl ether in 140 ml of tetrahydrofuran within 1.5 hours. After 1 hour at 40° C. it is cooled to 0° C. mixed with 13 g of copper(I) chloride, stirred for 0.5 hour at 0° C., a solution of 10 g of 3,3- (2,2-dimethyltrimethylenedioxy) -5α, 10α-epoxy -14,17-ethanoestr-9(11)-en-17-ol (Scholz, S. et al., Liebigs Ann. Chem., (1989), p. 151 (13b)) is instilled in 80 ml of tetrahydrofuran and stirring is continued for 0.5 hour at 0° C. Then, a saturated ammonium chloride solution is added, stirred for 0.25 hour at 0° C., diluted with ethyl acetate, washed with sodium chloride solution, and evaporated to dryness in a vacuum. 14.2 g of crude 11β-(11-(dimethyl-tert-butylsilyloxy)-undecyl)-3,3-(2,2-dimethyltrimethylenedioxy)-14,17-ethanoestr-9-ene-5α, 17β-diol is obtained. The crude 11β-(11-(dimethyl-tert-butylsilyloxy)-undecyl) -3,3-(2,2-dimethyltrimethylenedioxy)-14,17-ethanoestr-9-ene-5α, 17β-diol is stirred in 70 ml of tetrahydrofuran with 80 ml of glacial acetic acid and 40 ml of water for 1.5 hours at 50° C. bath temperature. Then, it is diluted with ethyl acetate, washed four times with sodium bicarbonate and common salt solution, dried on sodium sulfate, evaporated to dryness in a vacuum and chromatographed on silica gel with hexane/ethyl acetate. 4.8 g of 14,17-ethano-11β-(11-hydroxyundecyl)-17-hydroxyestra-4,9-dien-3-one, $[\alpha]^{22}_D = -121.1°$, is obtained as oil.

d) 11-(14,17-Ethano-17-hydroxy-3-oxoestra-4,9-dien-11β-yl)-undecanoic acid-N-methyl-N-isopropyl)-amide 1.0 g of 14,17-ethano-11β-(11-hydroxyundecyl)-17-hydroxyestra-4,9-dien-3-one is slowly mixed with 1.0 ml of Jones reagent in 17 ml of acetone at 0° C. and stirred for 1 hour. For working up, 1.5 ml of 2-propanol is added, evaporated to dryness in a vacuum, 0.1 n hydrochloric acid is added, extracted four times with dichloromethane, washed with common salt solution, dried on sodium sulfate and evaporated to dryness in a vacuum. 860 mg of crude 11-(14,17-ethano-17-hydroxyestra-4,9-dien-3-on11β-yl)-undecanoic acid is obtained as foam.

The crude 11-(14,17-ethano-17-hydroxyestra-4,9-dien-3-on-11β-yl)-undecanoic acid is stirred in 15 ml of dichloromethane at −10° C. with 0.22 ml of N-methylmorpholine and 0.25 ml of chloroformic acid isobutyl ester for 0.5 hour. Then, 0.27 ml of N-methyl-N-isopropylamine is slowly instilled and stirred for 1 hour at 25° C. For working up, it is mixed with sodium bicarbonate solution, diluted with dichloromethane, washed with water and common salt solution, dried on sodium sulfate, evaporated to dryness in a vacuum and chromatographed on silica gel with dichloromethane/acetone. 655 mg of 11-(14,17-ethano-17-hydroxy -3-oxoestra-4,9-dien- 11β-yl)-undecanoic acid-(N-methyl-N-isopropyl)-amide, $[\alpha]^{22}_D = -106.1°$, is obtained as oil.

e) 11-( 14,17-Ethano-3,17-dihydroxyestra-1,3,5 (10)-trien-11β-yl)-undecanoic acid-(N-methyl-N-isopropyl)-amide 500 mg of 11-(14,17-ethano-17-hydroxy-3-oxoestra-4,9-dien-11β-yl)-undecanoic acid-(N-methyl-N-isopropyl)-amide in 7 ml of dichloromethane is slowly mixed at 0° C. with a solution of 0.26 ml of acetyl bromide in 0.51 ml of acetic anhydride and stirred for 16 hours at 25° C. Then, it is diluted with dichloromethane, washed with sodium bicarbonate solution, water and common salt solution, dried on sodium sulfate and evaporated to dryness in a vacuum. Crude 11-(3,17-diacetoxy-14,17-ethanoestra-1,3,5(10)-trien-11β-yl)-undecanoic acid-(N-methyl-N-isopropyl)-amide is obtained as oil.

This crude product is stirred in 10 ml of a in methanolic potassium hydroxide solution for 1 hour at 25° C. Then, it is neutralized with in hydrochloric acid, concentrated by evaporation in a vacuum, added to water, extracted four times with dichloromethane, washed with common salt solution, dried on sodium sulfate, evaporated to dryness in a vacuum and chromatographed on silica gel with dichloromethane/acetone. Pure 11-(14,17-ethano-3,17-dihydroxyestra-1,3,5(10)-trien-11βyl)-undecanoic acid-(N-methyl-N-isopropyl)-amide, $[\alpha]^{22}_D = +54.8°$, is obtained as colorless crystals of melting point 126°–128° C.

EXAMPLE 2

11-(14,17-Ethano-3,17-dihydroxyestra-1,3,5(10)-trien-11β-yl)-undecanoic acid-(N-methyl-N-2,2,3,3,4,4,4-heptafluorobutyl)-amide a) 11-(14,17-Ethano-17-hydroxy-3-oxoestra-4,9-dien-11β-yl)-undecanoic acid-(N-methyl-N-2,2,3,3,4,4,4-heptafluorobutyl)-amide 860 mg of crude 11-(14,17-ethano-17-hydroxyestra-4,9-dien-3-on-11β-yl)-undecanoic acid is stirred in 15 ml of dichloromethane at −10° C. with 0.22 ml of N-methylmorpholine and 0.25 ml of chloroformic acid isobutyl ester for 0.5 hour. Then, 0.27 ml of N-methyl-N-2,2,3,3,4,4,4-heptafluorobutylamine is slowly instilled and stirred for 1 hour at 25° C. For working up, it is mixed with sodium bicarbonate solution, diluted with dichloromethane, washed with water and common salt solution, dried on sodium sulfate, evaporated to dryness in a vacuum and chromatographed on silica gel with dichloromethane/acetone. 581 mg of 11-(14,17-ethano-17-hydroxy-3-oxoestra-4,9-dien-11 β-yl )-undecanoic acid-(N-methyl-N-2,2,3,3,4,4,4-heptafluorobuty)-amide, $[\alpha]^{22}_D = -119.2°$, is obtained as oil b) 11-(14,17-Ethano-3,17-dihydroxyestra-1,3,5(10)-trien-11β-yl)-undecanoic acid-(N-methyl-N-2,2,3,3,4,4,4-heptafluorobutyl)-amide 500 mg of 11-(14,17-ethano-17-hydroxy-3-oxoestra-4,9-dien-11β-yl)-undecanoic acid-(N-methyl-N-2,2,3,3,4,4,4-heptafluorobutyl)-amide in 7 ml of dichloromethane is slowly mixed at 0° C. with a solution of 0.26 ml of acetyl bromide in 0.51 ml of acetic anhydride and stirred for 16 hours at 25° C. Then, it is diluted with dichloromethane, washed with sodium bicarbonate solution, water and common salt solution, dried on sodium sulfate and evaporated to dryness in a vacuum. Crude 11(3,17-diacetoxy-14,17-ethanoestra-1,3,5(10)-trien-11β-yl)-undecanoic acid-(N-methyl-N-2,2,3,3,4,4,4-heptafluorobutyl)-amide is obtained as oil.

This crude amide is stirred in 10 ml of a in methanolic potassium hydroxide solution for 1 hour at 25° C. Then, it is neutralized with in hydrochloric acid, concentrated by evaporation in a vacuum, added to water, extracted four times with dichloromethane, washed with common salt solution, dried on sodium sulfate, evaporated to dryness in a vacuum and chromatographed on silica gel with dichloromethane/acetone. Pure 11-(14,17-ethano-3,17-dihydroxyestra-1,3,5(10)-trien-11β-yl)-undecanoic acid-(N-methyl-N-2,2,3,3,4,4,4-heptafluorobutyl)-amide, $[\alpha]^{22}_D = +67.1°$ is obtained as colorless oil.

EXAMPLE 3

14,17-Ethano-11β-(11-N-methyl-N-isopropylaminoundecyl)- estra-1, 3, 5(10)-triene-3,17-diol a) 14,17-Ethano-17-hydroxy-11β-(11-N-methyl-N-isopropylaminoundecyl)-estra-4,9-dien-3-one 1.0 g of 14,17-ethano-17-hydroxy-11β-(11-hydroxyundecyl)-estra-4,9-dien-3-one in 17 ml of dichloromethane is stirred at −10° C. with 0.22 ml of N-methylmorpholine and 0.25 ml of chloroformic acid isobutyl ester for 0.5 hour. Then, 0.27 ml of N-methyl-N-isopropylamine is slowly instilled and stirred for 1 hour at 25° C. For working up, it is mixed with sodium bicarbonate solution, diluted with dichloromethane, washed with water and common salt solution, dried on sodium sulfate, evaporated to dryness in a vacuum and chromatographed on silica gel with dichloromethane/acetone. 702 mg of 14,17-ethano-17-hydroxy-11β-(11-N-methyl-N-isopropylaminoundecyl)-estra-4,9-dien-3-one 3-one, $[\alpha]^{22}_D = -55.3°$ is obtained as oil b) 14,17-Ethano-11β-(11-N-methyl-N-isopropylaminoundecyl)-esta-1,3,5(10)-triene-3,17-diol 500 mg of 14,17-ethano-17-hydroxy-11β-(11-N-methyl-N-isopropylaminoundecyl)-estra-4,9-dien-3 -one in 7 ml of dichloromethane is slowly mixed at 0° C. with a solution of 0.26 ml of acetyl bromide in 0.51 ml of acetic anhydride and stirred for 16 hours at 25° C. Then, it is diluted with dichloromethane, washed with sodium bicarbonate solution, water and common salt solution, dried on sodium sulfate and evaporated to dryness in a vacuum. Crude 3,17-diacetoxy-14,17-ethano-11β-(11-N-methyl-N-isopropylaminoundecyl)-estra-1,3,5(10) -triene is obtained as oil.

This crude product is stirred in 10 ml of a in methanolic potassium hydroxide solution for 1 hour at 25° C. Then, it is neutralized with in hydrochloric acid, concentrated by evaporation in a vacuum, added to water, extracted four times with dichloromethane, washed with common salt solution, dried on sodium sulfate, evaporated to dryness in a vacuum and chromatographed on silica gel with dichloromethane/acetone. Pure 14,17-ethano-11β-(11-N-methyl-N-isopropylaminoundecyl)-estra-1,3,5(10)-triene-3, 17-diol, $[\alpha]^{22}_D = +39.4°$, is obtained as foam.

EXAMPLE 4

9-(14,17-Ethano-3,17-dihydroxyestra-1,3,5(10)-trien-11βyl)-nonyl-4,4,5,5,5-pentafluoropentyl-sulfoxide
a) 4,4,5,5,5-Pentafluoropentanol A solution of 25 g of 4,4,5,5,5-pentafluoropent-2-en-1-ol (Kitazume, T. and Ishikawa, N.J. Am. Chem. Soc., (1985), p. 5186) in 100 ml of ethyl acetate is shaken with 100 mg of platinum dioxide under a hydrogen atmosphere for 1 hour. Then, the catalyst is filtered off and distilled fractionating. At 133°–135° C., 22 g of 4,4,5,5,5-pentafluoropentanol is obtained with $^1$H-NMR (CDCl$_3$) δ: 1.86 (m, H2), 2.18 (m, H1) and 3.75 (t, J=6.1 Hz, H1).
b) 4,4,5,5,5-Pentafluoropentylmercaptan 65 ml of azodicarboxylic acid ethyl ester is stirred with a solution of 107 g of triphenylphosphine in 800 ml of tetrahydrofuran for 0.5 hour, then 30 ml of thioacetic acid as well as 20 g of 4,4,5,5,5-pentafluoropentanol in 100 ml of tetrahydrofuran are slowly added and stirred for 1 hour at 0° C. as well as overnight at 25° C. and distilled fractionating under reduced pressure. The 4,4,5,5,5-pentafluoropentyl-1-thioacetate thus obtained is stirred with 100 ml of a 2 n sodium hydroxide solution for 3 hours at 100° C. cooled with 2 n hydrochloric acid, brought to pH 4, extracted with diethyl ether, washed with common salt solution, dried on sodium sulfate and concentrated by evaporation in a vacuum. 15 g of crude 4,4,5,5,5pentafluoropentylmercaptan is obtained as oil.

c) 9-Bromononyl-4,4,5,5,5-pentafluoropentyl-sulfide 30 ml of azodicarboxylic acid ethyl ester is stirred with a solution of 50 g of triphenylphosphine in 400 ml of tetrahydrofuran for 0.5 hour, then 10 g of crude 4,4,5,5, 5pentafluoropentylmercaptan as well as 12 g of 9-bromononanol in 48 ml of tetrahydrofuran are slowly added and stirred for 1 hour at 0° C. as well as overnight at 25° C. For working up, it is concentrated by evaporation in a vacuum and chromatographed on silica gel with hexane/ethyl acetate. 14 g of 9-bromononyl-4,4,5,5,5-pentafluoropentyl-sulfide is obtained as pale yellow oil. d) 9-(14,17-Ethano-17-hydroxy-3-oxoestra-4,9-dien-11β-yl)-nonyl-4,4,5,5,5-pentafluoropentyl-sulfoxide 0.6 g of magnesium chips is introduced in 6 ml of tetrahydrofuran and mixed with a solution of 10 g of 9-bromononyl-4,4,5,5,5-pentafluoropentyl-sulfide in 14 ml of tetrahydrofuran within 15 hours After 1 hour at 40° C. it is cooled to 0° C. mixed with 0 13 g of copper (I) chloride, stirred for 0.5 hour at 0° C., a solution of 1.0 g of 3,3-(2, 2-dimethyltrimethlyenedioxy)-5α, 10α-epoxy-14,17-ethanostr-9(11)-ene-5α, 17β-diol (Scholz, S. et al., Liebigs Ann. Chem., (1989), p. 151 (13b)) is instilled in 8 ml of tetrahydrofuran and stirring is continued for 0.5 hour at 0° C. Then, it is added with a saturated ammonium chloride solution, stirred for 0.25 hour at 0° C. diluted with ethyl acetate, washed with sodium chloride solution and evaporated to dryness in a vacuum. 1.3 g of crude 9-(3,3-(2,2-dimethyltrimethylenedioxy)-14,17-ethano-5,17-dihydroxyestr-9-en-11β-yl)-nonyl-4,4,5,5,5-pentafluoropentyl-sulfide is obtained.

The crude sulfide is stirred in 7 ml of tetrahydrofuran with 8 ml of glacial acetic acid and 4 ml of water for 1.5 hours at 50° C. bath temperature. Then, it is diluted with ethyl acetate, washed four times with sodium bicarbonate and common salt solution, dried on sodium sulfate, evaporated to dryness in a vacuum, dissolved in 15 ml of methanol, treated with 440 mg of sodium periodate, diluted with ethyl acetate, washed four times with sodium bicarbonate and common salt solution, dried on sodium sulfate, evaporated to dryness in a vacuum and chromatographed on silica gel with hexane/ethyl acetate. 985 mg of 9-(14,17-ethano17-hydroxy-3-oxoestra-4,9-dien-11β-yl)-nonyl-4,4,5,5,5-pentafluoropentyl-sulfoxide, $[\alpha]^{22}_D 32 -75.3°$, is obtained as oil e) 9-(14,17-Ethano-3,17-dihydroxyestra-1,3,5(10)-trien-11β-yl)-nonyl-4,4,5,5,5 -pentafloropentyl-sulfoxide 500 mg of 9-(14,17-ethano-17-hydroxyestra-4,9-dien-3-on-11βyl)-nonyl-4,4,5,5,5-pentafluoropentyl-sulfoxide in 7 ml of dichloromethane is slowly mixed at 0° C. with a solution of 0.26 ml of acetyl bromide in 0.51 ml of acetic anhydride and stirred for 2 hours at 25° C. Then, it is diluted with dichloromethane, washed with sodium bicarbonate solution, water and common salt solution, dried on sodium sulfate and evaporated to dryness in a vacuum. Crude 9-(3,17-diacetoxy-14,17-ethanoestra-1,3,5(10)-trien-11β-yl)-nonyl-4,4,5,5,5-pentafluoropentyl-sulfoxide is obtained as oil.

This crude product is stirred in 10 ml of a in methanolic potassium hydroxide solution for 1 hour at 25° C. Then, it is neutralized with in hydrochloric acid, concentrated by evaporation in a vacuum, added to water, extracted four times with dichloromethane, washed with common salt solution, dried on sodium sulfate, evaporated to dryness in a vacuum and chromatographed on silica gel with dichloromethane/acetone. Pure 9-(14,17-ethano-3,17-dihydroxyestra-1,3,5(10)-trien-11β-yl)-nonyl-4,4,5,5,5-pentafluoropentyl-sulfoxide, $[\alpha]^{22}_D = +43.2°$, is obtained as colorless oil.

EXAMPLE 5

10-(14,17-Ethano-3,17-dihydroxyestra1,3,5(10)-trien-11β-yl)-decanoic acid-(N-methyl-N-isopropyl)-amide According to the method of example 1, by using 10-bromodecyl-tert-butyldimethylsilyl ether instead of 11-bromoundecyl-tert-butylidimethylsilyl ether, the 11-(14, 17-ethano-3,17-dihydroxyestra-1,3,5(10)-trien-11β-yl)-decanoic acid-(N-methyl-N-isoprophyl)-amide is obtained as colorless crystals of melting point 112°–114° C.

EXAMPLE 6

12-(14,17-Ethano-3,17-dihydroxyestra-1,3,5(10)-trien-11β-yl)-dodecanoic acid-(N-methyl-N-isopropyl)-amide According to the method of example 1, by using 12-bromododecyl-tert-butyldimethylsilyl ether instead of 11-bromoundecyl-tert-buthyldimethylsilyl ether, the G11-(14,17-ethano-3,17-dihydroxyestra-1,3,5(10)-trien-11β-yl)-decanoic acid-(N-methyl-N-isopropyl)-amide is obtained as colorless crystals of melting point 107°–109° C.

EXAMPLE 7

11-(3-Benzoyloxy-14,17-ethano-17-hydroxyestra-1,3, 5(10)-trien-11β-yl)-undecanoic acid-(N-methyl-N-isopropyl)-amide 1.0 g of 11-(14,17-ethano-3,17-dihydroxyestra-1,3,5(10)-trien-11βyl)-undecanoic acid-(N-methyl-N-isopropyl)-amide is mixed in 11.3 ml of acetone at 0° C. with 3.2 ml of 0.1 n sodium hydroxide solution and 0.3 ml of benzoyl chloride and stirred for 0.5 more hour at 0° C. For working up, it is added to sodium bicarbonate, extracted three times with ethyl acetate, washed with common salt solution, dried on sodium sulfate, evaporated to dryness in a vacuum and chromatographed on silica gel with hexane/ethyl acetate. 1.0 g of 11-(3-benzoyloxy-14,17-ethano-17-hydroxyestra-1,3, 5(10)-trien-11β-yl)-undecanoic acid-(N-methyl-N-isopropyl)-amide, $[\alpha]^{22}_D = +42.1°$, is obtained as foam.

EXAMPLE 8

11-(14,17-Ethano-17-hydroxy-3-methoxyestra-1,3,5(10)-trien-11β-yl)-undecanoic acid-(N-methyl-N-isopropyl)-amide 1.0 g of 11-(14,17-ethano-3,17-dihydroxyestra-3,5(10)-trien-11β-yl)-undecanoic acid-(N-methyl-N-isopropyl)-amide is mixed in 10 ml of acetone with 3 g of potassium carbonate and 0.3 ml of methyl iodide and stirred for 5 more hours at 50° C. For working up, it is added to sodium bicarbonate solution, extracted three times with ethyl acetate, washed with common salt solution, dried on sodium sulfate, evaporated to dryness in a vacuum and chromatographed on silica gel with hexane/ethyl acetate. 1.0 g of 11-(14,17-ethano-17-hydroxy-3-methoxyestra-l,3,5(10)-trien-11β-yl)-undecanoic acid-(N-methyl-N-isopropyl)-amide $[\alpha]^{22}_D = +56.8°$, is obtained as foam.

The compound of example 4 can also be produced according to the invention as described below:

9-(14,17-Ethano-3,17-dihydroxyestra-1,3,5(10)-trien-11β-yl)-nonyl-4,4,5,5,5-pentafluoropentyl-sulfoxide.

a) 4,4,5,5,5-Pentafluoropentanol

A solution of 25 g of 4,4,5,5,5-pentafluoropent-2-en-1-ol (Kitazume, T. and Ishikawa, N., J. Am. Chem. Soc., (1985), p. 5186) in 100 ml of ethyl acetate is shaken with 100 mg of platinum dioxide under a hydrogen atmosphere for 1 hour. Then, the catalyst is filtered off and distilled fractionating. At 133°–135° C. 22 g of 4,4,5,5,5-pentafluoropentanol is obtained with $^1$H-NMR (CDCl$_3$) δ: 1.86 (m, H2), 2.18 (m, H1) and 3.75 (t, J=6.1 Hz, H1 ) .

b) Thioacetic acid-S-(4,4,5,5,5-pentafluoropentyl)-ester

A solution of 17.3 g of 4,4,5,5,5-pentafluoropentanol in 40 ml of pyridine is mixed at 0° C. with 21 g of tosyl chloride and stirred for 3 hours at 0° C. For working up, the reaction mixture is added to 2 n sulfuric acid, extracted with diethyl ether, washed neutral with water, dried on sodium sulfate and concentrated by evaporation in a vacuum. 32.7 g of crude toluene-4-sulfonic acid-4,4,5,5,5-pentafluoropentyl ester is obtained as oil. The latter is dissolved in 300 ml of acetone and refluxed with 23 g of potassium thioacetate for 18 hours at 100° C. bath temperature. Then, it is mixed with water, extracted with diethyl ether, washed with water, dried on sodium sulfate, concentrated by evaporation in a vacuum and distilled. At 173°–177° C., 15 g of thioacetic acid-S-(4, 4,5,5,5-pentafluoropentyl)-ester is obtained.

c) 14,17-Ethano-11β-(11-hydroxynonyl)-17-hydroxyestra-4,9-dien-3-one 8.5 g of magnesium chips is introduced in 85 ml of tetrahydrofuran and mixed with a solution of 125 g of 9-bromononyl-tert-butyldimethylsilyl ether in 150 ml of tetrahydrofuran within 15 hours After 1 hour at 40° C. it is cooled to 0° C. mixed with 15 g of copper(I) chloride, stirred for 0 5 hour at 0° C., a solution of 33 g of 3,3- (2,2-dimethyltrimethylenedioxy)-5α, 10α-epoxy-14,17-ethanoestr-9(11)-en-17-ol (Scholz, S. et al., Liebigs Ann. Chem., (1989), p. 151 (13b)) is instilled in 150 ml of tetrahydrofuran and stirring is continued for 0.5 hour at 0° C. Then, a saturated ammonium chloride solution is added, stirred for 0 25 hour at 0° C. diluted with ethyl acetate, washed with sodium chloride solution and evaporated to dryness in a vacuum. 49.2 g of crude 11β-(9-(dimethyl-tert-butylsilyloxy)-nonyl)-3,3-(2,2-dimethyltrimethylenedioxy)-14,17-ethanoestr-9-ene-5α, 17β -diol is obtained. The crude 11β-(11-(dimethyl-tert-butylsilyloxy)-nonyl)-3,3-(2,2-dimethyltrimethylenedioxy)-14,17-ethanoestr-9-ene-5α, 17β-diol is stirred in 180 ml of tetrahydrofuran with 206 ml of glacial acetic acid and 103 ml of water for 2.5 hours at 50° C. bath temperature. Then, it is diluted with ethyl acetate, washed four times with sodium bicarbonate and common salt solution, dried on sodium sulfate, evaporated to dryness in a vacuum and chromatographed on silica gel with hexane/ ethyl acetate. 17.8 g of 14,17-ethano-11β-(11-hydroxynonyl)-17-hydroxyestra-4,9-dien-3-one, $[\alpha]^{22}_D = -116.5°$, is obtained as foam.

d) 17-Acetoxy-11β-(9-acetoxynonyl)-14,17-ethanoestra-1, 3,5(10)-trien-3-ol 20 ml of acetic anhydride and 400 mg of dimethylaminopyridine are added to a solution of 4.8 g of 14,17-ethano-11β-(11-hydroxynonyl)-17-hydroxyestra-4,9- dien-3-one in 40 ml of pyridine and stirred for 4 hours at room temperature. Then, the reaction solution is added to a hydrochloric acid mixture of ice water/common salt, extracted with ethyl acetate, washed neutral, dried on sodium sulfate and concentrated by evaporation in a vacuum. 4.8 g of crude 17-acetoxy-11β-(9-acetoxynonyl)-14, 17-ethanoestra-4,9 -dien-3is obtained, which is stirred in 75 ml of ethanol with 1.5 g of 10% palladium on carbon for 21 hours at 100° C. bath temperature. Then, it is filtered on Celite, concentrated by evaporation in a vacuum and chromatographed on silica gel with hexane/ethyl acetate. 1.2 g of pure 17-acetoxy-11β-(9-acetoxynonyl)-14,17-ethanoestra-1,3,5(10)-trien-17-ol is obtained.

e) 3-Benzoyloxy-14,17-ethano-11β-(9-tosyloxynonyl)-estra-1,3,5(10)-trien-3-ol

Pure 17-acetoxy-11β-(9-acetoxynonyl)-14,17-ethanoestra-1,3,5(10)-trien-3-ol (800 mg) is stirred with 8 ml of in methanolic potassium hydroxide solution for 2 hours at room temperature, added to water, acidified with 2 n hydrochloric acid, extracted three times with ethyl acetate, dried on sodium sulfate and concentrated by evaporation in a vacuum. 670 mg of crude 14,17-ethano-11β-(9-hydroxynonyl)-estra-1,3,5(10)-triene-3,17-diol is obtained, which is dissolved in 9.3 ml of acetone, mixed with 2.28 ml of in sodium hydroxide solution, drop by drop with 0.18 ml of benzoyl chloride and stirred for 0.5 hour. Then, it is extracted three times with ethyl acetate, washed neutral, dried on sodium sulfate and concentrated by evaporation in a vacuum. 830 mg of crude 3-benzoyloxy-14,17-ethano-11β-(9-hydroxynonyl)-estra-1,3,5(10) -trien-17-ol is obtained. A solution of 830 mg of 3-benzoyloxy-14,17-ethano-11β-(9-hydroxynonyl)-estra-1,3,5(10)-trien-17-ol in 10 ml of pyridine is stirred with 763 mg of tosyl chloride for 4.5 hours at room temperature. Then, it is diluted with ethyl acetate, washed with 1 n hydrochloric acid, washed neutral with water, dried on sodium sulfate, concentrated by evaporation in a vacuum and chromatographed on silica gel with hexane/ethyl acetate. 480.6 mg of pure 3-benzoyloxy-14,17-ethano-11β-(9-tosyloxynonyl)-estra-1,3,5(10)-trien-17-ol is obtained as foam.

f) 14,17-Ethano-11β-[9-(4,4,5,5,5-pentafluoropentylsulfanyl)-nonyl]-estra-1,3,5(10)-triene-3,17-diol A solution of 207 mg of thioacetic acid-S-(4,4,5,5,5-pentafluoropentyl)-ester in 3 ml of methanol is stirred for 0.5 hour with 60 mg of sodium methoxide at room temperature. This solution is instilled in a solution of 480 mg of 3-benzoyloxy-14.17-ethano-11β-(9-tosyloxynonyl)-estra-1,3,5(10)-trien-17-ol in 10 ml of dimethylformamide and stirred for another 3 hours at room temperature. Then, it is added to 0.1 n hydrochloric acid, extracted three times with ethyl acetate, washed with water, dried on sodium sulfate, concentrated by evaporation in a vacuum and chromatographed on silica gel with hexane/ethyl acetate. 251 mg of 14,17-ethano-11β-[9-(4,4,5,5,5-pentafluoropentylsulfanyl)-nonyl]-estra-1,3,5(10)-triene-3, 17-diol is obtained as oil.

g) 9-(14,17-Ethano-3,17-dihydroxyestra-1,3,5(10)-trien-11β-yl)-nonyl-4,4,5,5,5-pentafluoropentyl-sulfoxide A solution of 130 mg of 14,17-ethano-11β-[9-(4,4,5,5,5-pentafluoropentylsulfanyl)-nonyl]-estra-1,3,5(10)-triene-3, 17diol in 5 ml of methanol is stirred with 0.2 ml of water and 56.2 mg of sodium periodate for 4.5 hours at room temperature. Then, it is added to water, extracted with ethyl acetate, washed with 1 n hydrochloric acid, washed neutral with water, dried on sodium sulfate, concentrated by evaporation in a vacuum, dissolved in hot hexane and precipitated by cooling. 84.7 mg of pure 9-(14,17-ethano-3,17-dihydroxyestra-1,3,5(10)-trien-11β-yl)-nonyl-4,4,5,5, 5-pentafluoropentyl-sulfoxide is obtained.

We claim:

1. An 11β-substituted 14,17-ethanoestratriene compound of formula I

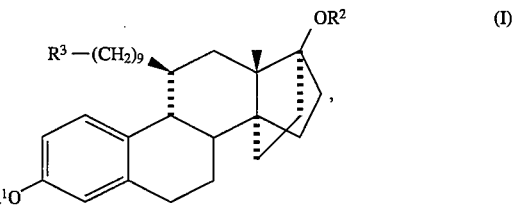

wherein $R^1$ is hydrogen, $C_1$–$C_{12}$ alkanoyl, benzoyl, straight-chain or branched-chain $C_1$–$C_{12}$ alkyl, $C_3$–$C_7$ cycloalkyl, or $C_4$–$C_8$ alkylcycloalky, $R^2$ is hydrogen a $C_1$–$C_{12}$ alkanoyl, $R^3$ is

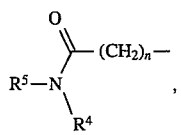

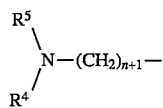

or $R^4$—SO—, n is 0, 1 or 2, and $R^4$ and $R^5$ are each, independently of one another, hydrogen, straight-chain or branched $C_1$–$C_8$ alkyl or partially fluorinated straight-chain or branched $C_1$–$C_8$ alkyl.

2. A compound according to claim 1, wherein $R^1$ is H, acetyl, propionyl, methyl, ethyl, cyclopropyl, cyclopentyl, cyclohexyl, methylcyclopropyl or methycyclopentyl.

3. A compound according to claim 1, wherein $R^2$ is H, acetyl or propionyl.

4. A compound according to claim 1 wherein $R^4$ and $R^5$ are each, independently, H, straight-chain or branched $C_{1-8}$-alkyl, 2,2,3,3,4,4,4-heptafluorobutyl or 4,4,5,5,5-pentafluoropentyl.

5. A compound according to claim 1, wherein $R^1$ is H, acetyl, propionyl, methyl, ethyl, cyclopropyl, cyclopentyl, cyclohexyl, methylcyclopropyl or methylcyclopentyl; $R^2$ is H, acetyl or propionyl; and $R^4$ and $R^5$ are each, independently, H, straight-chain or branched $C_{1-8}$-alkyl, 2,2,3,3,4, 4,4-heptafluorobutyl or 4,4,5,5,5-pentafluoropentyl.

6. A pharmaceutical composition comprising at least one compound according to claim 1 and a pharmaceutically compatible.

7. A pharmaceutical composition according to claim 6, wherein the amount of said compound is 5–500 mg.

8. A compound according to claim 1, wherein said compound is:

11-(14,17-ethano-3,17-dihydroxyestral-1,3,5(10)-trien-11β-yl)-undecanoic acid-(N-methyl-N-isoprophly)-amide, 11-(14,17-ethano-3,17-dihydroxyestra-1,3,5(10)-trien-11β-yl)-undecanoic acid-(N-methyl-N-2,2,3,3,4,4,4,-heptafluorobutyl)-amide, 14,17-ethano-11β-(11-N-methyl-N-isopropylaminoundecyl)-estra-1,3,5(10)-triene-3,17-diol, 9-(14,17-ethano-3,17-dihydroxyestra-1,3,5(10)-trien-11β-yl)-nonyl- 4,4,5,5,5-pentafluoropentyl-sulfoxide, 10-(14,17-ethan-3,17-dihydroxyestra, 1,3,5(10)-triene-11β-yl)-decanoic acid-(N-methyl-N-isopropyl)-amide.

12-(14,17-ethano-3,17-dihydryestra-1,3,5(110)-trien-11β-yl)-dodecanoic acid- (N-methyl-N-isgpropyl)-amide, or 11 -(3-benzoyloxy-14,17-ethano-17-hydroxyestra- 1,3,5(10)-trien-11β-yl)-undecanoic acid-(N-methyl-N-isopropyl)-amide, or 11-(14,17-ethano-17-hydroxy-3-methoxyestra-1,3,5(10)-trien-11β-yl)-undecanoic acid- (N-methyl-N-isopropyl)-amide.

9. A pharmaceutical composition comprising at least one compound according to claim 8 and a pharmaceutically compatible vehicle.

10. A pharmaceutical composition according to claim 9, wherein the amount of said compound is 5–500 mg.

11. A method of treating a patient suffering from an estrogen-dependent disease comprising administering to said patient an effective amount of a compound according to claim 1.

12. A method according to claim 11, wherein said disease is anovulatory infertility.

13. A method according to claim 11, wherein said disease is prostatic hyperplasia.

14. A method according to claim 11, wherein said disease is breast cancer.

15. A method according to claim 11, wherein said disease is endometrial cancer.

16. A method according to claim 11, wherein said disease is melanoma.

17. A method according to claim 11, wherein said compound is administered in a daily dose of 0.1–25 mg/kg.

* * * * *